US00PP18072P2

(12) United States Plant Patent
Dekker

(10) Patent No.: US PP18,072 P2
(45) Date of Patent: Sep. 25, 2007

(54) ***CHRYSANTHEMUM* PLANT NAMED 'DEKALLCREAM'**

(50) Latin Name: *Chrysanthemum×morifolium*
Varietal Denomination: Dekallcream

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 11/358,830

(22) Filed: Feb. 17, 2006

(51) Int. Cl.
*A01H 5/00* (2006.01)

(52) U.S. Cl. ..... Plt./256

(58) Field of Classification Search ..... Plt./256
See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Chrysanthemum* plant named 'Dekallcream', characterized by its daisy-type inflorescences with elliptic-shaped, light yellow-colored ray florets; typically grown as a spray-type; strong and upright flowering stems; freely flowering habit; early and uniform flowering response; and good postproduction longevity.

2 Drawing Sheets

Botanical designation: *Chrysanthemum×morifolium.*
Cultivar denomination: 'Dekallcream'.

BACKGROUND OF THE INVENTION

The present invention relates to a new and distinct cultivar of *Chrysanthemum* plant, botanically known as *Chrysanthemum×morifolium* and referred to by the name 'Dekallcream'.

The new *Chrysanthemum* is a naturally-occurring whole plant mutation of the *Chrysanthemum×morifolium* cultivar Dekallwhite, not patented. The new *Chrysanthemum* was discovered and selected by the Inventor in September, 2004 as a single flowering plant within a population of plants of the cultivar Dekallwhite in a controlled environment in Hensbroek, The Netherlands.

Asexual reproduction of the new *Chrysanthemum* by terminal cuttings harvested in Hensbroek, The Netherlands since November, 2004, has shown that the unique features of this new *Chrysanthemum* are stable and reproduced true to type in successive generations.

BRIEF SUMMARY OF THE INVENTION

The cultivar Dekallcream has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dekallcream'. These characteristics in combination distinguish 'Dekallcream' as a new and distinct cultivar:

1. Daisy-type inflorescences with elliptic-shaped, light yellow-colored ray florets; typically grown as a spray-type.
2. Strong and upright flowering stems.
3. Freely flowering habit.
4. Early and uniform flowering response.
5. Good postproduction longevity.

Plants of the new *Chrysanthemum* can be compared to plants of the parent, the cultivar Dekallwhite. In side-by-side comparisons conducted in Hensbroek, The Netherlands, plants of the new *Chrysanthemum* differed from plants of the cultivar Dekallwhite primarily in ray floret coloration as plants of the cultivar Dekallwhite have white-colored ray florets.

Plants of the new *Chrysanthemum* can be compared to plants of the *Chrysanthemum* cultivar Yen Yellow, not patented. In side-by-side comparisons conducted in Hensbroek, The Netherlands, plants of the new *Chrysanthemum* differed primarily from plants of the cultivar Yen Yellow in the following characteristics:

1. Plants of the new *Chrysanthemum* were more vigorous than plants of the cultivar Yen Yellow.
2. Branching habit of plants of the new *Chrysanthemum* was broader than branching habit of plants of the cultivar Yen Yellow.
3. Plants of the new *Chrysanthemum* had larger inflorescences than plants of the cultivar Yen Yellow.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum.*

The photograph on the first sheet comprises a side perspective view of a typical flowering stem of 'Dekallcream'.

The photograph at the top of the second sheet comprises a close-up view of typical inflorescences of 'Dekallcream'.

The photograph at the bottom of the second sheet is a close-up view of the upper and lower surfaces of typical inflorescences and leaves of 'Dekallcream'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown during the summer in Hensbroek, The Netherlands, under commercial practice in a glass-covered greenhouse. Plants were initially given long day/short night treatments followed by short day/long night treatments to induce flower initiation and development. During the production of the plants, day temperatures ranged from 17.5° C. to 30° C., night temperatures ranged from 18.5° C. to 24° C. and light levels were about five kilolux. Plants were pinched once and were about nine weeks from planting when the photographs and the description were taken.

Botanical classification: *Chrysanthemum×morifolium* cultivar Dekallcream.

Commercial classification: Daisy-type *Chrysanthemum* typically grown as a spray-type cut flower.

Parentage: Naturally-occurring whole plant mutation of the *Chrysanthemum×morifolium* Dekallwhite, not patented.

Propagation:

*Type.*—Terminal tip cuttings.

*Time to initiate roots, summer.*—About 6 days at 20° C.

*Time to initiate roots, winter.*—About 7 days at 20° C.

*Time to produce a rooted cutting, summer.*—About 14 days at 20° C.

*Time to produce a rooted cutting, winter.*—About 16 days at 20° C.

*Root description.*—Fine and freely branching; light brown in color.

Plant description:

*Appearance.*—Herbaceous daisy-type cut *Chrysanthemum;* typically grown as a spray-type; erect and strong flowering stems. Moderately vigorous growth habit.

*Flowering stem description.*—Length: About 90 cm. Diameter: About 6 mm. Strength: Strong. Texture: Pubescent. Aspect: Erect. Branching habit: Plants are typically grown as single stems. Color: Close to 146B.

*Foliage description.*—Arrangement: Alternate; simple. Length: About 5 cm to 7.5 cm. Width: About 3 cm to 4 cm. Apex: Cuspidate. Base: Attenuate. Margin: Palmately lobed. Texture, upper and lower surface: Pubescent. Petiole length: About 5 mm to 10 mm. Color: Developing and fully expanded foliage, upper surface: Close to 147A; venation, 146A to 146B. Developing and fully expanded foliage, lower surface: Close to 147B; venation, close to 146B. Petiole, upper and lower surfaces: Close to 146B.

Inflorescence Description:

*Appearance.*—Daisy-type inflorescence form with elliptic-shaped ray florets. Inflorescences borne on terminals above foliage. Disk and ray florets develop acropetally on a capitulum. Inflorescences not fragrant. Typically grown as spray-types.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 6.5 weeks later. Early and uniform flowering response.

*Postproduction longevity.*—Cut inflorescences will maintain good substance and form for about four weeks.

*Quantity of inflorescences per flowering stem.*—About 30 inflorescence buds and inflorescences per flowering stem.

*Inflorescence size.*—Diameter: About 3 cm to 3.5 cm. Depth (height): About 1 cm. Diameter of disc: About 1 cm.

*Inflorescence buds.*—Height: About 3 mm to 4 mm. Diameter: About 5 mm to 6 mm. Shape: Flattened spherical. Color: 137C to 137D.

*Ray florets.*—Length: About 1.2 cm to 1.5 cm. Width: About 4 mm to 6 mm. Shape: Elliptic. Apex: Rounded to cuspidate. Base: Attenuate; fused. Margin: Entire. Texture, upper and lower surfaces: Smooth, glabrous; satiny. Number of ray florets per inflorescence: About 35 to 40 in about two whorls. Color: When opening, upper surface: 4B. When opening, lower surface: 4C. Fully opened, upper surface: 7D. Fully opened, lower surface: 4D.

*Disc florets.*—Shape: Tubular; elongated. Length: About 2 mm to 3 mm. Width: About 0.5 mm to 1 mm. Number of disc florets per inflorescence: About 75. Color: Immature: Close to 16B. Mature: Apex: Close to 145B. Mid-section: Close to 15B. Base: 145C to 145D.

*Peduncles.*—Length, terminal peduncle: About 2 cm. Length, fourth peduncle: About 3.5 cm. Diameter: About 1 mm to 1.5 mm. Angle: About 45° from vertical. Strength: Strong. Texture: Pubescent. Color: Close to 137D.

*Reproductive organs.*—Androecium: Not observed on disc florets. Gynoecium: Stigma length: About 3 mm. Stigma width: About 0.2 mm. Stigma color: Towards the apex, close to 151C; towards the base, close to 150C.

*Seed/fruit.*—Seed and fruit production has not been observed.

Disease/pest resistance: Resistance to pathogens and pests of *Chrysanthemum* has not been observed on plants of the new *Chrysanthemum.*

It is claimed:

1. A new and distinct cultivar of *Chrysanthemum* plant named 'Dekallcream', as illustrated and described.

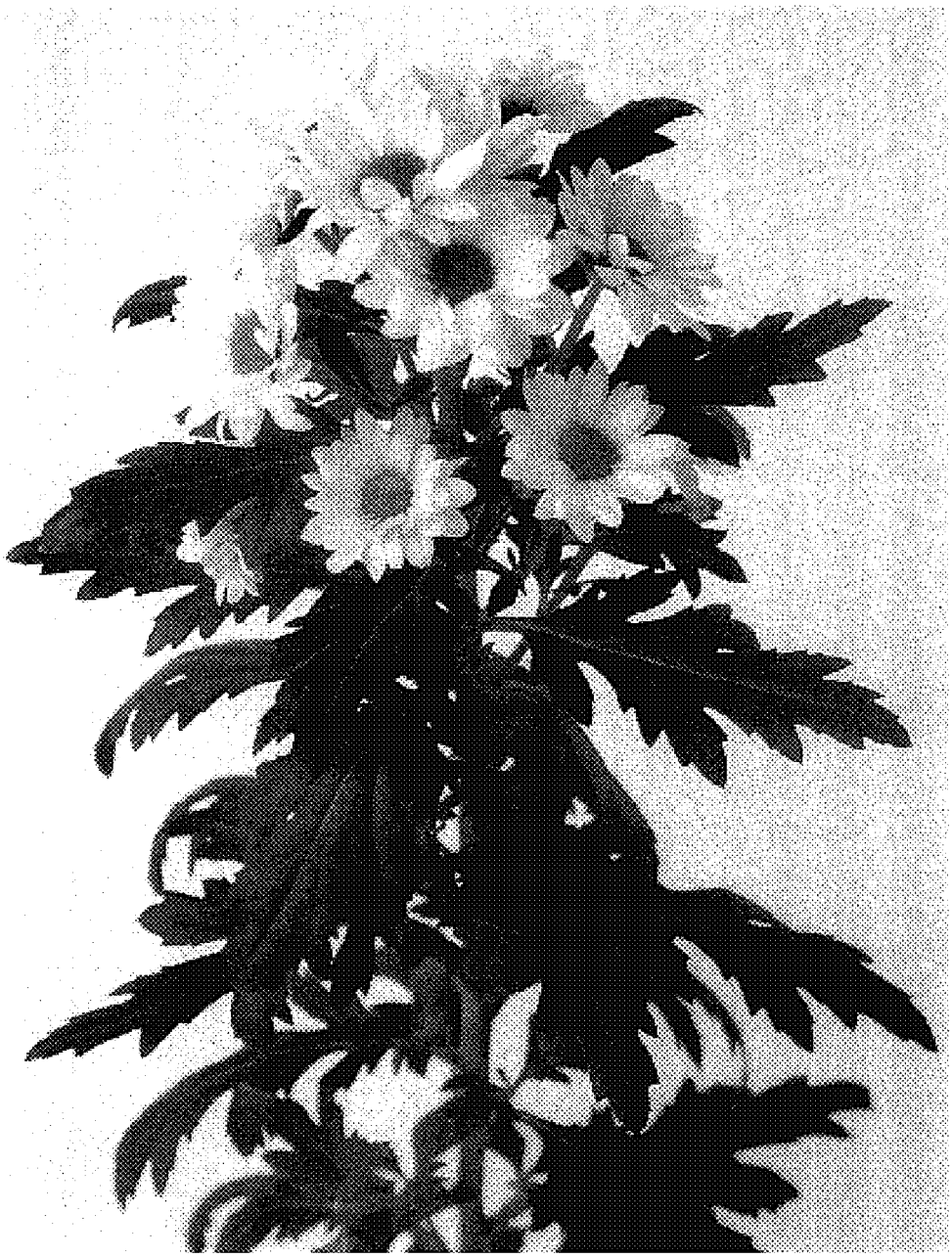

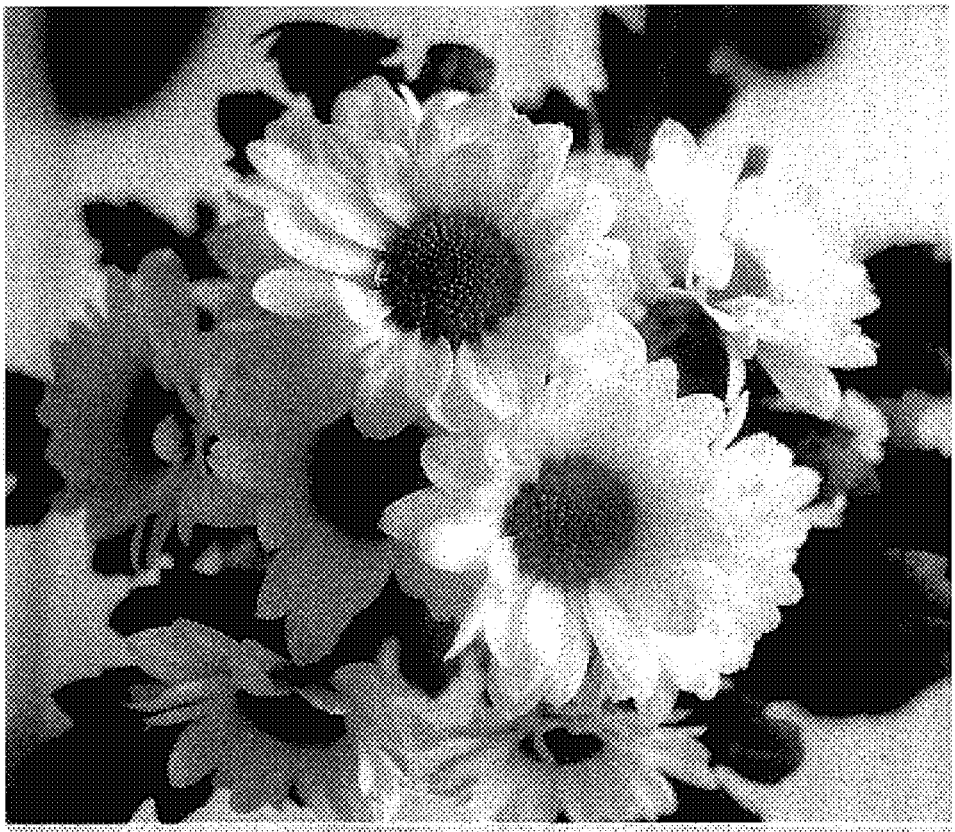
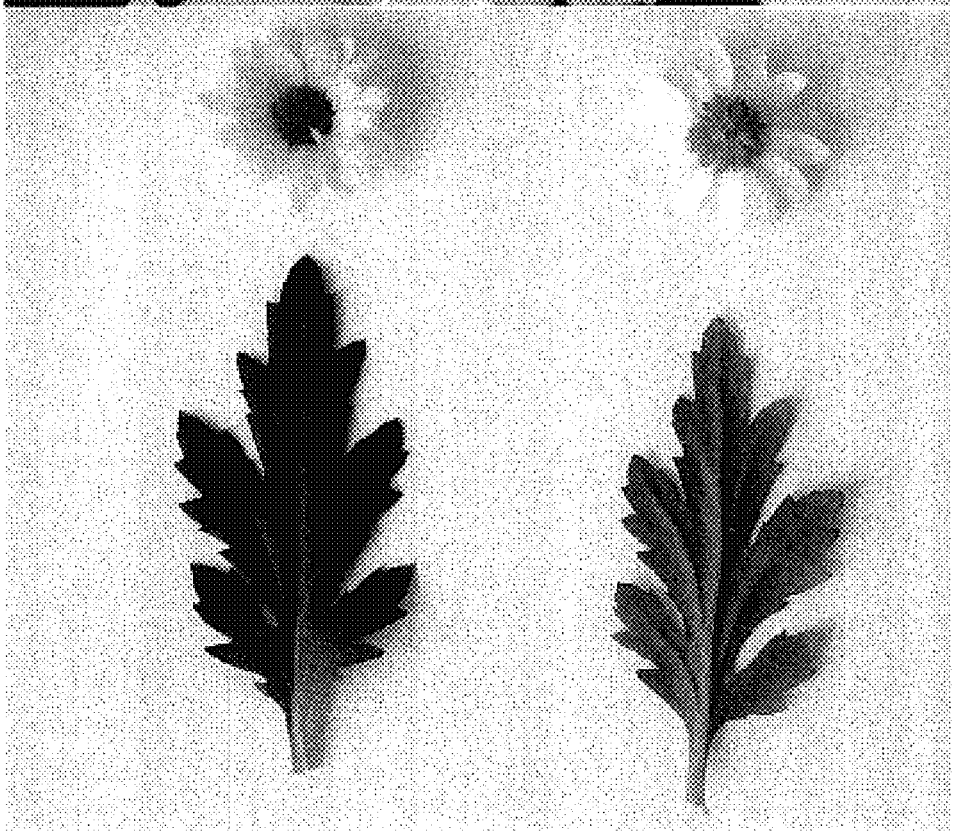

* * * * *